(12) United States Patent
Gillick et al.

(10) Patent No.: US 9,517,151 B2
(45) Date of Patent: Dec. 13, 2016

(54) CONTROL OF BALLOON INFLATION RATE DURING DEPLOYMENT OF SCAFFOLD

(75) Inventors: Matthew Gillick, Murrieta, CA (US);
Yunbing Wang, Sunnyvale, CA (US);
Justin Mann, Murrieta, CA (US);
Bruce Wilson, Temecula, CA (US);
James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 281 days.

(21) Appl. No.: 13/436,527

(22) Filed: Mar. 30, 2012

(65) Prior Publication Data

US 2013/0261729 A1    Oct. 3, 2013

(51) Int. Cl.
*A61F 2/958* (2013.01)
*A61M 25/10* (2013.01)

(52) U.S. Cl.
CPC .......... *A61F 2/958* (2013.01); *A61M 25/1018* (2013.01); *A61M 25/10181* (2013.11); *A61M 25/10185* (2013.11); *A61F 2250/0013* (2013.01)

(58) Field of Classification Search
CPC .............. A61F 2/958; A61F 2240/0013; A61F 2250/0013; A61F 2/2433; A61M 25/10; A61M 25/1018; A61M 2039/2413; A61M 25/104
USPC .............. 606/108, 192–194; 623/1.11–1.15; 604/96.01, 97.01, 99.01
See application file for complete search history.

(56) References Cited

U.S. PATENT DOCUMENTS

| | | | |
|---|---|---|---|
| 3,841,319 A | 10/1974 | Michael et al. | |
| 5,078,681 A | 1/1992 | Kawashima | |
| 5,634,910 A * | 6/1997 | Kanner et al. | 604/208 |
| 5,685,848 A * | 11/1997 | Robinson et al. | 604/97.03 |
| 5,749,851 A | 5/1998 | Wang | |
| 5,893,868 A | 4/1999 | Hanson et al. | |
| 5,993,416 A * | 11/1999 | Choh et al. | 604/99.02 |
| 6,419,657 B1 | 7/2002 | Pacetti | |
| 6,547,760 B1 * | 4/2003 | Samson et al. | 604/103.01 |
| 7,537,580 B2 * | 5/2009 | Willard | 604/96.01 |
| 7,799,048 B2 * | 9/2010 | Hudson et al. | 606/199 |
| 8,162,902 B2 * | 4/2012 | Adams | 604/247 |
| 2003/0078538 A1 | 4/2003 | Neale et al. | |
| 2005/0288764 A1 * | 12/2005 | Snow et al. | 623/1.11 |
| 2006/0118189 A1 | 6/2006 | Tekulve et al. | |
| 2011/0319866 A1 | 12/2011 | Consigny et al. | |

FOREIGN PATENT DOCUMENTS

DE    39 35579    5/1991

OTHER PUBLICATIONS

International Search Report and Written Opinion for PCT/US2013/034139, mailed Sep. 2, 2013, 13 pgs.

* cited by examiner

*Primary Examiner* — Julian W Woo
*Assistant Examiner* — Lucas Paez
(74) *Attorney, Agent, or Firm* — Squire Patton Boggs (US) LLP

(57) ABSTRACT

An apparatus and method for controlling inflation pressure and pressurization rate of a balloon during deployment of a stent or scaffold are disclosed. The apparatus and method involve a pressure attenuator for controlling an inflation rate of the delivery balloon.

8 Claims, 4 Drawing Sheets

CONTROL OF BALLOON INFLATION RATE DURING DEPLOYMENT OF SCAFFOLD

BACKGROUND OF THE INVENTION

Field of the Invention

This invention relates to a method and apparatus for deployment of a stent or scaffold in the treatment of coronary and peripheral artery disease.

Description of the State of the Art

This invention relates generally to methods of treatment with radially expandable endoprostheses that are adapted to be implanted in a bodily lumen. An "endoprosthesis" corresponds to an artificial device that is placed inside the body. A "lumen" refers to a cavity of a tubular organ such as a blood vessel. A scaffold is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter so that they can be delivered to and deployed at a treatment site.

Stents are typically implanted by use of a catheter which is inserted at an easily accessible location and then advanced through the vasculature to the deployment site. The stent is initially maintained in a radially compressed or collapsed state to enable it to be maneuvered through a body lumen. Once in position, the stent is usually deployed either automatically by the removal of a restraint, actively by the inflation of a balloon about which the stent carried on the deployment catheter, or both.

In reference to balloon catheter stents, the stent is mounted on and crimped to the balloon portion the catheter. The catheter is introduced transluminally with the stent mounted on the balloon and the stent and balloon are positioned at the location of a lesion. The balloon is then inflated to expand the stent to a larger diameter to implant it the artery at the lesion. An optimal clinical outcome requires correct sizing and deployment of the stent.

An important aspect of stent deployment is the rapidity with which the stent is expanded. For balloon deployed stents, this is controlled by balloon inflation. Inflation is usually achieved through manual inflation/deflation devices (indeflators) or an indeflator unit that possesses some automation.

Stents made from biostable or non-degradable materials, such as metals that do not corrode or have minimal corrosion during a patient's lifetime, have become the standard of care for percutaneous coronary intervention (PCI) as well as in peripheral applications, such as the superficial femoral artery (SFA). Such stents, especially antiproliferative drug coated stents, have been shown to be capable of preventing early and later recoil and restenosis.

It has been recognized for metal stents that slower inflation is better. During inflation, kinetic effects create non-equilibrium conditions. For example, the friction of the balloon against the stent is affected by inflation rate. A fast inflation/deflation cycle can result in higher levels of stent recoil. Inflation speed affects the uniformity of stent deployment along its length. Often, the distal and proximal ends of the balloon inflate first. A dumbbell or dog bone shape is created which exerts a net inward force on the stent. Consequently, fast stent inflation may lead to more stent shortening. Ideally, the stent is deployed uniformly, with an even spreading of the struts around the periphery. Fast deployment is believed to increase the likelihood of struts being clustered together in sections and over expanded in others.

Additionally, there are many potential reasons why inflation speed affects stent expansion. Catheter balloons can be folded in a non-uniform way. Balloon folds can get stuck or "caught" on stent struts. The lesion environment is rarely uniform, or with a perfectly concentric plaque. Lesions are typically eccentric, sometimes with fibrous or calcified focal regions. Consequently, the resistance to radial expansion of the balloon may be greater in certain directions resulting in an eccentric deployment. Lastly, in clinical practice, the process of stent implantation can become routine. Such familiarity often leads to shorter procedural times which tend to beneficial for the patient except for steps, such as stent inflation, where faster is not always better.

In order to effect healing of a diseased blood vessel, the presence of the stent is necessary only for a limited period of time, as the artery undergoes physiological remodeling over time after deployment. A bioresorbable stent or scaffold obviates the permanent metal implant in vessel, allowing late expansive luminal and vessel remodeling, leaving only healed native vessel tissue after the full resorption of the scaffold. Stents fabricated from bioresorbable, biodegradable, bioabsorbable, and/or bioerodable materials such as bioabsorbable polymers can be designed to completely absorb only after or some time after the clinical need for them has ended. Some or all of the reasons for a slower inflation rate for metallic stent may also apply to balloon expandable polymer stents or scaffolds. In addition, more importantly, for a polymer material, due to its viscoelastic property, tends to become more and more rigid when it is deformed at a faster rate, which makes it critical to control the inflation rate of a polymeric stent to prevent any potential formation of cracks and broken struts.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a system for deployment of a stent comprising: a delivery balloon; a catheter comprising an inflation lumen in fluid communication with the delivery balloon, wherein a proximal end of the catheter is adapted to be connected to an inflation device, wherein the connection allows the inflation device to inject inflation fluid into the inflation lumen of the catheter to inflate the delivery balloon; and a pressure attenuator for controlling an inflation rate of the balloon, the pressure attenuator comprising a chamber connected with the inflation lumen of the catheter, wherein a movable containing wall of the chamber allows the volume of the chamber to vary in response to pressure of inflation fluid that flows into the chamber from the inflation lumen, and wherein a biasing element associated with the movable containing wall that applies a biasing force opposing an increase in the volume of the chamber.

Various embodiments of the present invention include a method for deployment of a stent comprising: injecting an inflation fluid from a fluid source into an inflation lumen of a catheter in fluid communication with a delivery balloon to inflate the balloon, wherein a pressure of the fluid in the catheter and balloon increases as the fluid is injected; and controlling a rate of fluid pressure increase with a pressure attenuator comprising a chamber filled with inflation fluid from the inflation lumen; and allowing the chamber volume to vary to control the rate of fluid pressure increase, wherein the chamber volume varies in response to variation in the pressure of inflation fluid, wherein a biasing force modulates the variation in the chamber volume.

DETAILED DESCRIPTION OF THE INVENTION

Generally, the present invention includes methods of delivering and delivery systems for deploying stents in lumens or vessels. More specifically, the present invention relates to methods and systems for controlling the inflation rate of a balloon that deploys a stent.

The methods and systems are particularly applicable to, though not limited to, deployment of bioresorbable scaffolds. Such scaffolds can include a support structure in the form of a scaffold made of a material that is bioresorbable, for example, a bioresorbable polymer such as a lactide-based polymer. The scaffold is designed to completely erode away from an implant site after treatment of an artery is completed. The scaffold can further include a drug, such as an antiproliferative or anti-inflammatory agent. A polymer coating disposed over the scaffold can include the drug which is released from the coating after implantation of the stent. The polymer of the coating is may also be bioresorbable.

The present invention, however, is not limited for use with bioresorbable scaffolds or even stents. It is also applicable to various polymeric scaffolds/stents, metallic stents, stent-grafts, and generally tubular medical devices in the treatment of bodily lumens where is desirable to control the expansion of such devices in the lumens.

A stent or scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to supporting of the load imposed by radially inward directed forces. Structural elements, such as the linking elements or struts, are generally non-load bearing, serving to maintain connectivity between the rings. For example, a stent may include a scaffold composed of a pattern or network of interconnecting structural elements or struts.

Figure 1:
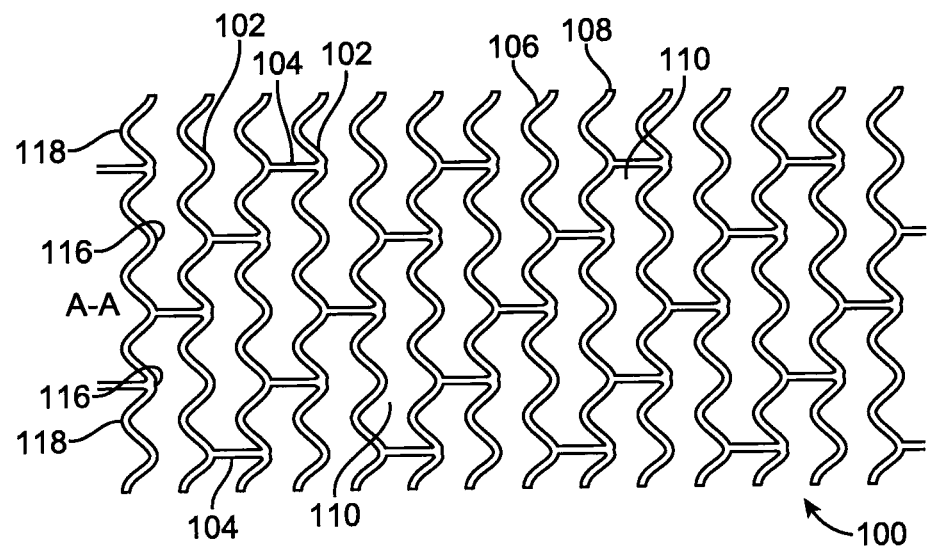
FIG. 1 illustrates a portion of an exemplary prior art stent or scaffold pattern shown in a flattened view.

FIG. 1 illustrates a portion of an exemplary stent or scaffold pattern 100 shown in a flattened view. The pattern 100 of FIG. 1 represents a tubular scaffold structure so that a cylindrical axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 form a plurality of cylindrical rings, for example, rings 106 and 108, arranged about the cylindrical axis A-A. The rings have an undulating or sinusoidal structure with alternating crests or peaks 116 and troughs or valleys 118. The rings are connected by the link struts 104. The scaffold has an open framework of struts and links that define a generally tubular body with gaps 110 in the body defined by rings and struts. A cylindrical tube may be formed into this open framework of struts and links by a laser cutting device that cuts such a pattern into a thin-walled tube that may initially have no gaps in the tube wall.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching.

Prior to insertion in the body, a bioresorbable scaffold, like a metallic stent, is tightly compressed onto a balloon. Plastic deformation of the crimped scaffold induced by the crimping process helps retain that the scaffold on the balloon. Once it is positioned at an implant site, the bioresorbable scaffold is expanded by the balloon. The expansion of the scaffold induces areas of plastic stress in the bioresorbable material to cause the scaffold to achieve and maintain the appropriate diameter on deployment.

An exemplary scaffold for coronary applications has the stent pattern described in US 2010/0004735. Other examples of stent patterns suitable for bioresorbable polymers are found in US 2008/0275537, specifically, the pattern depicted in FIG. 15.

A stent or scaffold delivery system includes a hollow catheter with an inflation lumen. A proximal end of the catheter has a catheter hub that connects to an inflation device, which can be an indeflator. The distal end of the catheter is connected to a stent-balloon assembly. As indicated above, prior to insertion into a patient, the balloon is in a deflated state in a low profile configuration with the stent crimped thereon. The inflation device has access to a source of inflation fluid.

Once the stent-balloon assembly is positioned at an implant site, the inflation device injects inflation fluid into the inflation lumen of the catheter. The fluid flows through the inflation lumen into the balloon. As fluid is injected into the inflation lumen and the balloon, the pressure therein increases with time, causing the balloon to inflate and expand the stent. Once the stent is fully expanded, the balloon is deflated and withdrawn from the implant site, leaving the stent at the implant site apposed against the vessel wall. The balloon is deflated by a negative pressure in the inflation lumen imposed by the inflation device which withdraws inflation fluid from the balloon.

An exemplary inflation device is the 20/30 Indeflator Inflation Device made by Abbott Vascular-Cardiac Therapies of Temecula, Calif., USA. The indeflator includes a pressure injector at a proximal end and an exit port at a distal end at the tip of a flexible tube that connects to a catheter hub. The inflation device has a chamber for holding inflation fluid for injecting into the catheter. The inflation device has a pressure gauge that measures the pressure of the injected inflation fluid.

The inflation fluid may assist a user in visualizing the catheter and balloon during delivery. A fluid that is visible to an imaging technique, such as x-ray fluoroscopy or magnetic resonance imaging (MRI), may be used to inflate a balloon. Such fluids are referred to as contrast agents. Thus, a contrast agent can include a radiopaque agent or a magnetic resonance imaging agent. "Radiopaque" refers to the ability of a substance to absorb x-rays. An MRI agent has a magnetic susceptibility that allows it to be visible with MRI.

Polymers that are stiff or rigid under conditions within a human body are promising for use as a scaffold material. Specifically, polymers that have a glass transition temperature (Tg) sufficiently above human body temperature, which is approximately 37° C., should be stiff or rigid upon implantation. For example, poly(L-lactide) (PLLA) or PLLA-based polymers have relatively high strength and stiffness at human body temperature.

The advantages of a slower inflation rate during deployment for metallic stents may also apply to bioresorbable scaffolds. The inventors have hypothesized that an additional reason for a slower inflation rate for polymer scaffolds or stents is that potential for damage (e.g., fracture, breaking of struts) to a polymer scaffold increases at higher inflation rate. In short, susceptibility of a polymer scaffold to damage may be a function of inflation rate. The potential for damage to a polymer scaffold at higher inflation rates may be greater than for metal stents.

Certain polymers may have suitable strength and stiffness properties, however, such polymers tend to have lower ultimate elongation (i.e., elongation at break) or ductility than metals. This potential weakness can be mitigated by a combination of scaffold design and polymer processing. Also, polymers (e.g., PLLA) exhibit viscoelastic behavior where the accumulated stress in the material is a function of the strain history, including the strain rate. Therefore, bioresorbable polymer scaffolds may be more susceptible to strut material damage as the inflation or expansion rate increases.

More specifically, for the bioresorbable scaffold disclosed above, the inventors have observed that deployment begins in end rings and propagates toward the middle. The inventors hypothesize that high rate of crest opening in the middle increases risk of premature fractures. The inventors further hypothesize that employing directional control on inflation will drive overall more consistent deployment speed and eliminate the potential for premature fractures.

The inventors have tested their hypothesis that bioresorbable polymer scaffolds may be more susceptible to damage at higher inflation rates. Bench tests on bioresorbable scaffolds were performed to evaluate the effect of inflation rate on damage. The scaffolds used in the test have a pattern similar to that shown in FIG. 15 of US 2008/0275537. The scaffolds are 3 mm in diameter and 18 mm long. The thickness and width of the scaffolds is about 150 microns. Detailed discussion of the manufacturing process of the bioresorbable scaffold can be found elsewhere, e.g., U.S. Patent Publication No. 2007/0283552.

As a surrogate for balloon inflation, the test involved moving two parallel pins apart that are disposed within and along the axis of a scaffold. As the pins were extended or moved apart, the load applied to the scaffold was measured as a function of extension of the pins. Four runs were performed at different rates to simulate different inflation rates. A discontinuity in the load vs. extension curves indicates the extension at which failure of ring struts occur. Table 1 below shows the extension at which ring struts fractured for each run. The data is Table 1 shows that as the extension rate increases, the extension at break or fracture of the scaffold decreases. These results imply that damage to a polymer scaffold depends on the inflation rate of a balloon during deployment. Specifically, it is expected that damage to scaffold will occur at lower deployment diameters as the inflation rate increases.

TABLE 1

Extension at fracture for polymer scaffolds for four runs with different extension rates.

| Run | Rate (mm/min) | Extension at All Ring PDTF ID* (mm) |
| --- | --- | --- |
| 1 | 0.254 | 6.522 |
| 2 | 2.54 | 6.073 |
| 3 | 25.4 | 5.527 |
| 4 | 254 | 5.325 |

*Post deployment to fracture inside diameter - deformation of scaffold is continued until broken.

It is believed that control of the inflation rate or average inflation rate below a certain value for at least a portion of the deployment process will prevent or mitigate scaffold damage during deployment. The inflation rate can be expressed in terms of the pressure of the inflation fluid within the inflation lumen and the balloon, for example, in psi/s.

Imposition of a maximum inflation rate might rely on physician training to achieve compliance. However, there is no guarantee that this inflation rate will be followed in clinical practice. Physicians are accustomed to stent devices that, while they have specific inflation rates dictated in the Instructions For Use, do not experience undue consequences if they are inflated faster than the specified inflation rates. For example, although there are reasons for a slower inflation rate for metals, the stress behavior of the material is not a strong function of strain rate, so stent damage is not as significant a concern.

Interventional procedures sometimes require a fast inflation of a balloon, stent, or scaffold. One reason would be the presence of a coronary perforation. Balloons by themselves, or balloons with scaffolds, are inflated rapidly to hold perforations closed and, hopefully, seal them. The patient may be experiencing other forms of duress such as ischemia induced angina, tachycardia, of fibrillation which pushes the physician to perform the procedure rapidly. Thus, there is a need for a systems and methods for control of scaffold inflation rate that does not rely on manual physician adjustment.

Embodiments of the present invention include delivery systems that incorporate a pressure attenuator connected to the inflation fluid path that controls the pressure of the inflation fluid. The pressure attenuator is in the form of a fluid accumulator. The rate of pressure increase or pressurization rate during all or part of the inflation process can be controlled by the accumulator to be within a specified pressurization rate range or below a maximum specified pressurization rate. The pressurization rate can controlled all the way up to the maximum deployment pressure, which is the maximum pressure reached during the deployment process. The maximum deployment pressure is typically reached when the scaffold deployment is complete and secure in the vessel.

During the inflation process, the pressure control by the accumulator may start only when the pressure exceeds a specified maximum pressure. During an initial stage of the inflation process, the balloon pressure is not high enough to expand or significantly expand the scaffold. Thus, there is little or no risk of scaffold damage due to high inflation rate since the scaffold either is not being expanded or experience only slight expansion. Therefore, prior to the start of pressure control by the accumulator, the pressurization rate can be higher than the maximum specified pressurization rate.

The maximum specified pressure may be about 2 atm, about 3 atm, about 4 atm, 2 to 4 atm, 2 to 3 atm, or 3 to 4 atm. During deployment below the maximum specified pressure, the pressurization rate can be up to 10 psi/s, up to 20 psi/s, about 30 psi/s, 10 to 20 psi/s, or 20 to 30 psi/s. The pressurization rate below the maximum specified pressure may be entirely under the control of the operator of the inflation device.

The average pressurization rate between the maximum specified pressure and the maximum deployment pressure may be controlled to be about 5 psi/s, about 6 psi/s, about 7 psi/s, about 8 psi/s, about 10 psi/s, 6 to 8 psi/s, 6 to 10 psi/s, 8 to 10 psi/s. The instantaneous pressurization rate may also be controlled to within these ranges.

The maximum deployment pressure can depend on the desired diameter of deployment. The maximum pressure may be about 7 atm, about 8 atm, about 10 atm, about 12 atm, about 14 atm, about 16 atm, 7 to 8 atm, 8 to 10 atm, or 10 to 16 atm.

The fluid accumulator can be connected to the inflation lumen between the proximal end of the catheter and the delivery balloon. Alternatively, the fluid accumulator can be connected to the inflation device. The accumulator may include a fluid chamber or reservoir defined by a structure or part of a structure with containing walls. For example, the structure may be a hollow tube. The volume of the chamber is variable and increases in response to an increase in pressure of fluid in the chamber. The volume varies due to a section of the containing walls being moveable. The movement of the section is modulated by a biasing element associated with the movable section that applies a biasing force that opposes movement that increases the volume of the chamber. The biasing element can be a spring that applies a compression force to the movable section that opposes the force arising from the pressure of the fluid in the chamber. An increase in pressure in the chamber causes the movable section to compress the spring, thereby increasing the volume of the chamber and allowing more fluid into the chamber.

Figure 2:
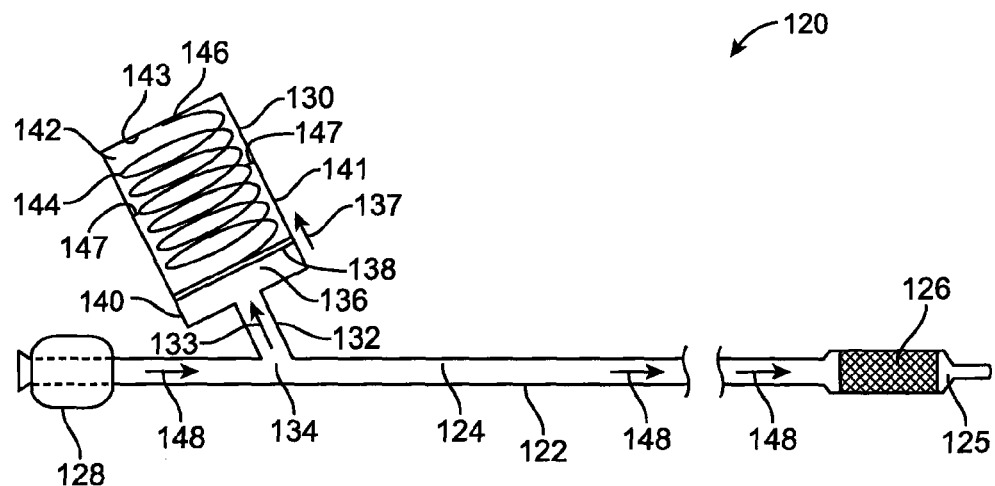
FIG. 2 depicts a cross-section of a delivery system that incorporates a pressure attenuator in the form of a fluid accumulator for controlling the inflation rate during deployment.

FIG. 2 depicts a cross-section of a delivery system 120 that incorporates a fluid accumulator 130 for controlling the inflation rate during deployment. Delivery system 120 includes a catheter 122 with an inflation lumen 124 through which inflation fluid flows. A deflated balloon 125 is connected to a distal end of catheter 122. A scaffold 126 is crimped over balloon 125. A proximal end of catheter 122 includes a catheter hub 128 that is adapted to be connected to an inflation device (not shown) that is configured to inject inflation fluid into inflation lumen 124 of catheter 122.

A fluid accumulator 130 is connected to catheter 122 by means of passage way 132. Fluid accumulator 130 is or is capable of fluid communication with inflation lumen 124 through passage way 132. Optionally, a pressure-actuated valve (not shown) can be incorporated in catheter 122, passage way 132, or fluid accumulator 130. The pressure actuated valve allows fluid to enter the chamber only when the pressure of the fluid in the catheter exceeds a specified maximum pressure.

A body of fluid accumulator 130 can be formed of a hollow tube 141 that includes a chamber 136 at the distal end of tube 141 for holding inflation fluid that flows from inflation lumen 124. Chamber 136 is defined by walls 140 of tube 141 and a movable wall or piston 138. Piston 138 separates chamber 136 from a compartment 142. A spring 144 is disposed within compartment 142. A distal end of spring 144 can apply a compression force to piston 138 on a surface opposite to chamber 136, and thus opposes movement of piston 138 is a direction shown by an arrow 137. A proximal end of spring 144 can apply a compression force on proximal interior surface 143 of the tube 141.

Prior to deploying stent 126 at an implant site, an inflation device (not shown) is affixed to catheter hub 128. An operator (physician) positions the stent and balloon at an implant site. The operator then manipulates the inflation device to pump inflation fluid into inflation lumen 124 which flows in the direction shown by arrows 148 into balloon 125. As the inflation fluid is injected, the pressure in inflation lumen 124 and balloon 125 increases.

The control of the pressurization rate of balloon 125 by fluid accumulator 130 can be delayed until for example, the pressure of the inflation fluid reaches a maximum specified value. One way of delaying such control is that during an initial time period after injection begins, inflation fluid is prevented from flowing into chamber 136 of fluid accumulator 130. During this time, the rate of injection and pressurization rate are completely controlled by adjustments made by the operator to the inflation device to inject inflation fluid.

When the pressure in the catheter is at or exceeds the specified maximum pressure, inflation fluid is allowed to flow through passage way 132, as shown by an arrow 133, into chamber 136. A pressure actuated valve may prevent flow until the specified maximum pressure is reached and then allow the flow above this pressure.

The pressure of the inflation fluid in chamber 136 applies a force on piston 138. If the force from the pressure is larger than the opposing compression force of spring 144, piston 138 moves, as shown by arrow 137, which increases the volume of chamber 136. The flow of fluid into chamber 136 and the variation in the volume of chamber 136 due to compression of spring 144 by piston 138 control the pressurization rate in catheter 122 and balloon 125. Specifically, the pressurization rate can be controlled by fluid accumulator 130 to be within a specified range or below a specified value. Therefore, above the specified maximum pressure, the pressurization rate depends on the adjustments by the operator and actions of fluid accumulator 130.

As an alternative to a pressure actuated valve, spring 144 may have a nonlinear compression force such that it has a higher or complete resistance to compression below the specified maximum pressure. Another alternative is that piston 138 may be configured to have a complete resistance or have a higher resistance to movement until the specified maximum pressure is reached.

Fluid accumulator 130 can control the pressurization rate to be within a specified pressurization rate range or less than a specified pressurization rate. For example, parameters such as the volume of chamber 136 and the compression force of the spring can be selected or adjusted to achieve a desired control of the pressurization rate. The compression force of the spring can be adjusted through selection of the stiffness of the spring. Increasing the volume of the chamber and decreasing the stiffness of the spring will control the pressurization rate to a lower value.

Once a maximum deployment pressure is reached, further spring compression can be prevented to stop control of the pressurization rate by fluid accumulator 130. This allows a rapid increase to a final post-dilation pressure. Further spring compression can be prevented, for example, by a hard stop 147 in compartment 142 that prevents further movement of piston 138 in the direction of arrow 137 when a surface of piston 138 engages hard stop 147. Hard stop 147 can be an inward protrusion in compartment 142.

Figure 3:
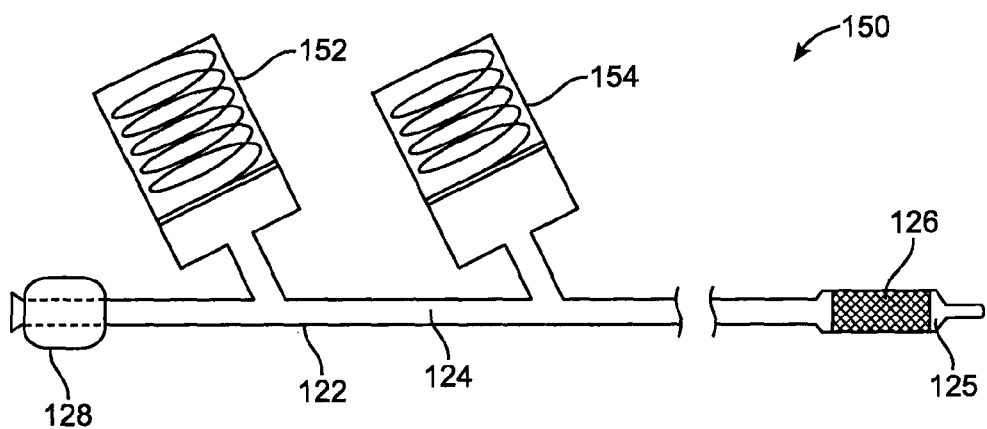
FIG. 3 depicts a cross-section of a delivery system that incorporates two fluid accumulators for controlling the inflation rate during deployment.

It may be desirable to use more than one fluid accumulator to control the pressurization rate. Several smaller fluid accumulators can be used rather than one large fluid accumulator. For example, a single fluid accumulator with a volume required for control of the pressurization rate may not fit into the sterile packaging designed for the stent-catheter assembly. FIG. 3 depicts a cross-section of a delivery system 150 that incorporates two fluid accumulators 152 and 154 for controlling the inflation rate during deployment. The function of each fluid accumulator is as described above. Each fluid accumulator can also have a pressure actuated valve. The different fluid accumulators can have the same chamber volume and spring constant. The specified maximum pressure of the pressure actuation valves can also be the same. Alternatively, the chamber volumes, spring constants, and specified actuation pressures can be different.

Figure 4A:
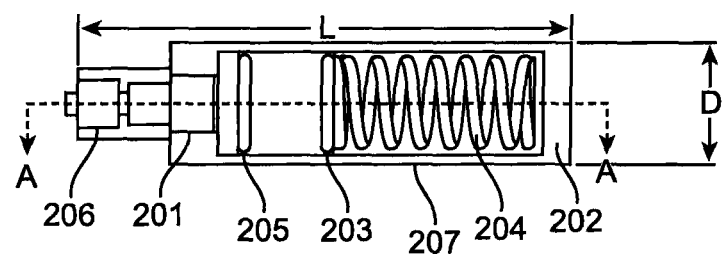
FIG. 4A depicts a detailed side view of a fluid accumulator.
Figure 4B:
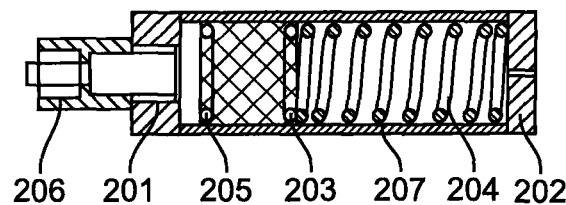
FIG. 4B depicts a detailed cross-sectional view of the fluid accumulator of FIG. 4B across line A-A.
Figure 4C:
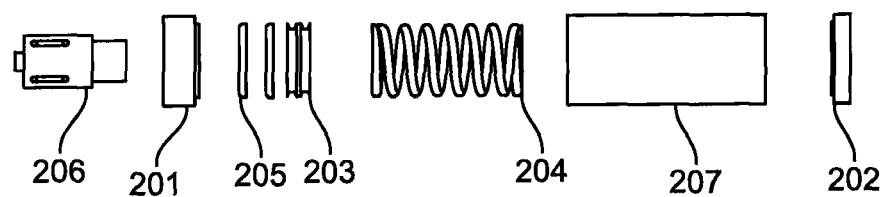
FIG. 4C is detailed side view of the fluid accumulator of FIGS. 4A-B showing component parts separated.

FIGS. 4A-B depict detailed views of a fluid accumulator. FIG. 4A is a side view and FIG. 4B is a cross-sectional view across line A-A. FIG. 4C is view of the fluid accumulator with component parts separated from one another. The fluid accumulator is composed of a plastic tube 207 with a compression spring 204 disposed within a proximal compartment of plastic tube 207. A proximal cap seals the proximal end of tube 207. A piston 203 is disposed within the tube distal to compression spring 204. A distal cap 201 and an O-Ring 205 seal the distal end of tube 207. An adapter 206 disposed within distal cap 201 is configured to connect to the inflation lumen of a catheter.

Example

Figure 5:
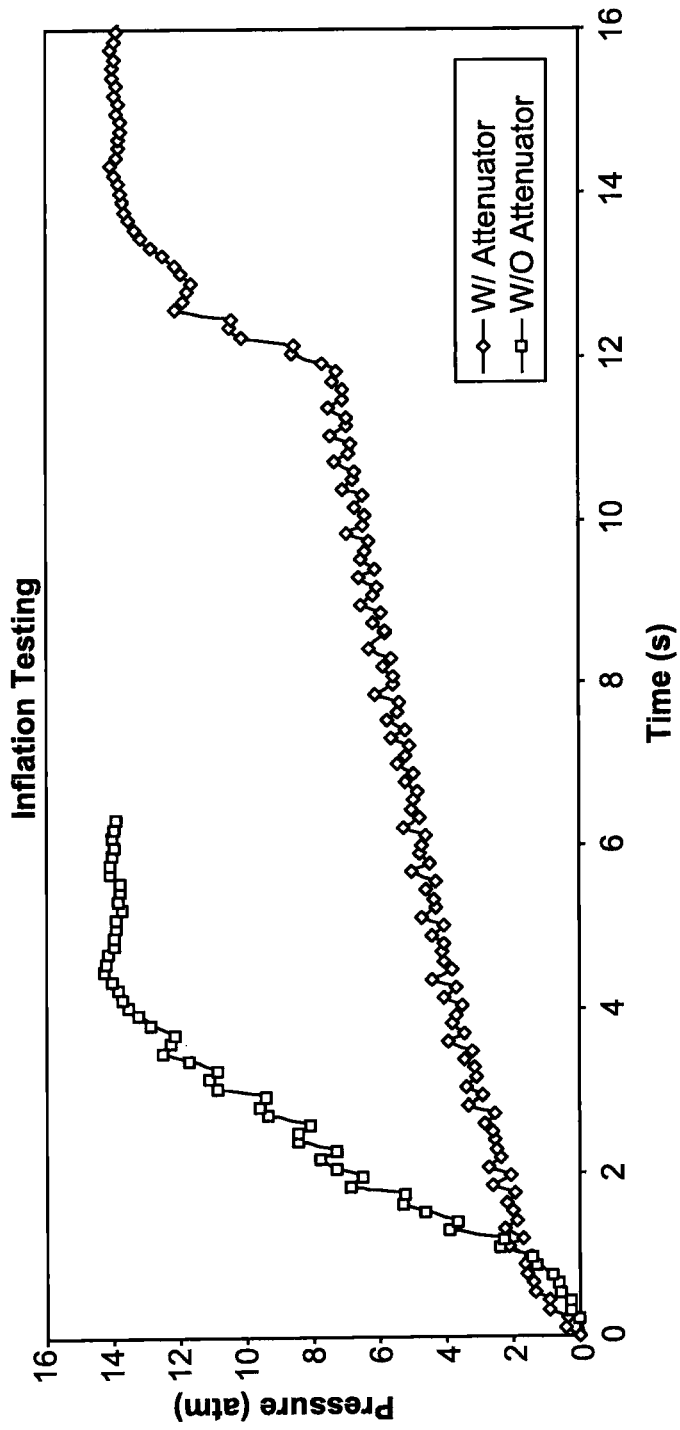
FIG. 5 shows the pressure during the deployment as a function of time for stent deployment runs without a fluid accumulator and with a fluid accumulator.

Bench tests of deployment of a bioresorbable scaffold with and without an attenuator were performed to evaluate the effect of a fluid accumulator on inflation rate. FIG. 5 shows the pressure during the deployment as a function of time. The slope of this curve is the pressurization rate. The results showed that the inflation rate was slowed down significantly with the attenuator between about 2 and 8 atm.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for deployment of a stent, the method comprising:
   injecting an inflation fluid from a fluid source into a hub of a catheter in fluid communication with a delivery balloon via an inflation lumen, the injecting causes the delivery balloon to be inflated by inflation fluid traveling through the inflation lumen, wherein a pressure of the inflation fluid in the inflation lumen and delivery balloon increases as the inflation fluid is injected;
   controlling a rate of fluid pressure increase with a pressure attenuator comprising a chamber filled with the inflation fluid from the inflation lumen, wherein controlling the rate of fluid pressure increase includes allowing a movable containing wall of the chamber to move from a starting position to a final position in response to accumulation of inflation fluid in the chamber and an increase in the pressure of the inflation fluid, and wherein the fluid communication between the hub of the catheter and the delivery balloon via the inflation lumen is present when the movable containing wall is at the starting position and the final position; and
   causing fluid pressure of the inflation fluid in the delivery balloon to increase after the movable containing wall is at the final position and with continued injection of inflation fluid into the hub.

2. The method of claim 1, wherein the inflation fluid is allowed to fill the chamber when the fluid pressure reaches a selected value.

3. The method of claim 1, wherein the rate of fluid pressure increase is controlled only when the fluid pressure reaches a selected value.

4. The method of claim 1, wherein as the fluid pressure is increased by the injection of the inflation fluid, the control of the rate of fluid pressure increase starts when the fluid pressure reaches a specified value.

5. The method of claim 1, further comprising depressurizing the inflation lumen after a maximum deployment pressure is reached, the maximum deployment pressure being a pressure that deploys a stent scaffold completely, wherein the pressure attenuator does not control the fluid pressure during depressurization.

6. The method of claim 1, wherein when controlling the rate of fluid pressure increase, a biasing force modulates the variation in the chamber volume.

7. The method of claim 6, wherein the biasing force is provided by a spring applying the biasing force to the movable containing wall of the chamber, and the biasing force opposes an increase in the chamber volume.

8. The method of claim 1, wherein when the movable containing wall is in the final position, inflation fluid is retained in the chamber.

* * * * *